United States Patent
Genin et al.

(10) Patent No.: US 6,825,225 B2
(45) Date of Patent: Nov. 30, 2004

(54) BICYCLIC ISOXAZOLINONES AS ANTIBACTERIAL AGENTS

(75) Inventors: Michael J. Genin, Paw Paw, MI (US); Michael Robert Barbachyn, Kalamazoo, MI (US); Jackson B. Hester, Jr., Galesburg, MI (US); Paul D. Johnson, Kalamazoo, MI (US); Fred L. Ciske, Lawton, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/991,134

(22) Filed: Nov. 14, 2001

(65) Prior Publication Data

US 2004/0116413 A1 Jun. 17, 2004

Related U.S. Application Data

(60) Provisional application No. 60/249,551, filed on Nov. 17, 2000.

(51) Int. Cl.[7] ..................... A61K 31/422; C07D 413/04
(52) U.S. Cl. ........................................ 514/380; 548/243
(58) Field of Search ........................... 548/243; 514/380

(56) References Cited

U.S. PATENT DOCUMENTS

| | | | |
|---|---|---|---|
| 4,965,268 A | 10/1990 | Wang et al. | 514/253 |
| 5,032,605 A | 7/1991 | Wang et al. | 514/376 |
| 5,036,092 A | 7/1991 | Wang et al. | 514/376 |
| 5,036,093 A | 7/1991 | Wang et al. | 514/376 |
| 5,039,690 A | 8/1991 | Wang et al. | 514/376 |
| 5,164,510 A | 11/1992 | Brickner | 548/231 |
| 5,684,023 A | 11/1997 | Riedl et al. | 514/337 |
| 5,792,765 A | 8/1998 | Riedl et al. | 514/236.8 |

FOREIGN PATENT DOCUMENTS

| | | | |
|---|---|---|---|
| WO | WO 99/64416 | 12/1999 | C07D/413/14 |
| WO | WO 99/64417 | 12/1999 | C07D/413/14 |
| WO | WO 00/10566 | 3/2000 | A61K/31/42 |
| WO | WO 00/21960 | 4/2000 | C07D/413/14 |

*Primary Examiner*—Laura L. Stockton
(74) *Attorney, Agent, or Firm*—John H. Engelmann; Lucy X. Yang

(57) ABSTRACT

The present invention provides compounds of formula I useful as anti microbial agents

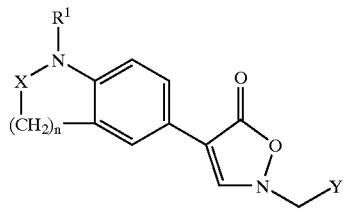

wherein X, Y, $R^1$, and n are as defined in thereof.

19 Claims, No Drawings

BICYCLIC ISOXAZOLINONES AS ANTIBACTERIAL AGENTS

CROSS-REFERENCE TO RELATED APPLICATION

This application claims the benefit of the following U.S. Provisional Application Ser. No. 60/249,551, filed Nov. 17, 2000, which is incorporated herein by reference in its entirety.

BACKGROUND OF THE INVENTION

The present invention relates to novel bicyclic isoxazolinones compounds and their preparations. These compounds are useful against a number of human and veterinary pathogens, including gram-positive aerobic bacteria such as multiply-resistant staphylococci and streptococci, anaerobic organisms such as bacteroides and clostridia species, and acid-fast organisms such as *Mycobacterium tuberculosis* and *Mycobacterium avium*.

INFORMATION DISCLOSURE

PCT publications, WO 99/64416, WO99/64417, and WO 00/21960 disclose isoxazolinone derivatives useful as antibacterial agents.

PCT publication, WO 00/10566 discloses isoxazolinones useful as antibacterial agents.

U.S. patent application Ser. No. 09/57216 discloses novel bicyclic isoxazolinones as antibacterial agents.

U.S. Pat. No. 5,164,510 discloses 5'-indolinyloxazolidin-2-ones of formula XI

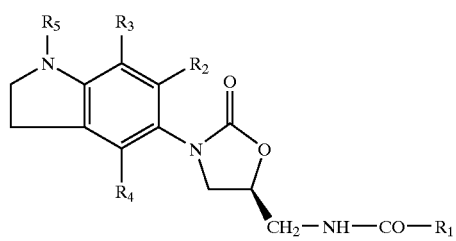

which are useful as antibacterial agents.

U.S. Pat. Nos. 5,036,092; 5,036,093; 5,039,690; 5,032,605 and 4,965,268 disclose aminomethyl oxazolidinyl aza cycloalkylbenzene derivatives useful as antibacterial agents.

U.S. Pat. Nos. 5,792,765 and 5,684,023 disclose substituted isoxazolinones useful as antibacterial agents.

SUMMARY OF THE INVENTION

The present invention provides a compound of formula I

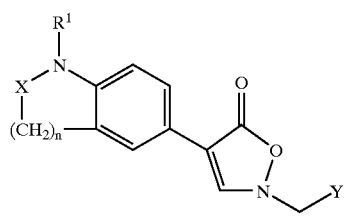

or a pharmaceutically acceptable salt thereof wherein

Y is
 a) —NHC(=W)$R^2$, or
 b) —O-het, —S-het, or —NH-het;

W is
 a) O, or
 b) S;

X is
 a) —S(=O)$_m$—, or
 b) —CH$R^3$—;

$R^1$ is
 a) $C_{1-8}$ alkyl,
 b) —C(=O)$R^4$, or
 c) —C(=S)NH$C_{1-4}$ alkyl;

$R^2$ is
 a) H,
 b) $C_{1-6}$ alkyl,
 c) cyclopropyl,
 d) —O$C_{1-4}$ alkyl,
 e) —NH$_2$,
 f) —NH$C_{1-6}$ alkyl, or
 g) —N($C_{1-6}$ alkyl)$_2$;

$R^3$ is H, or $C_{1-4}$ alkyl;

$R^4$ is
 a) H,
 b) $C_{1-6}$ alkyl,
 c) —CH$_2$OC(=O)$C_{1-4}$ alkyl;

at each occurrence above, alkyl is optionally substituted with one or more $R^5$;

$R^5$ is
 a) halo,
 b) CN,
 c) NO$_2$,
 d) $C_{1-6}$ alkyl,
 e) phenyl,
 f) O$R^6$,
 g) C(=O)$R^6$,
 h) OC(=O)$R^6$,
 i) C(=O)O$R^6$,
 j) S(=O)$_m R^6$,
 k) S(=O)$_m$N$R^6 R^6$,
 l) NHC(=O)$R^6$,
 m) C(=O)N$R^6 R^6$,
 n) N$R^6 R^6$, $R^6$ is independently H, $C_{1-6}$alkyl, phenyl, or het;

het is a C-linked five-(5) or six-(6) membered saturated or unsaturated heterocyclic ring having 1, 2, or 3 heteroatoms selected from the group consisting of oxygen, sulfur, and nitrogen, which is optionally fused to a benzene ring; wherein het is optionally substituted with one or more halo, CN, NO$_2$, $C_{1-6}$ alkyl, O$R^6$, phenyl, S(=O)$_m R^6$, C(=O)$R^6$, OC(=O)$R^6$,OC=O)$R^6$, NHC(=O)$R^6$, or N$R^6 R^6$, oxo, or oxime;

m is 0, 1 or 2; and n is 1 or 2.

In another aspect, the present invention also provides:

a pharmaceutical composition comprising a compound of formula I, or a pharmaceutically acceptable salt thereof, and a pharmaceutically acceptable excipient (the composition preferably comprises a therapeutically effective amount of the compound or salt), a method for treating gram-positive microbial infections in humans or other warm-blooded animals by administering to the subject in need a therapeutically effective amount of a compound of formula I, or a pharmaceutically acceptable salt thereof, a method for treating gram-negative microbial infections in humans or other warm-blooded animals by administering to the subject in need a therapeutically effective amount of a compound of formula I, or a pharmaceutically acceptable salt thereof.

The invention also provides some novel intermediates and processes disclosed herein that are useful for preparing compounds of formula I.

DETAILED DESCRIPTION OF THE INVENTION

The following definitions are used, unless otherwise described.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-7}$ alkyl refers to alkyl of one to seven carbon atoms, inclusive.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "O" for oxygen atom, "S" for sulfur atom, "N" for nitrogen atom, "h" for hour or hours and "rt" for room temperature).

It will be appreciated by those skilled in the art that compounds of the present invention may have a or more chiral centers and be isolated in optically active or racemic form. The present invention encompasses any racemic, optically-active (such as enantiomers, diastereomers), tautomeric, or stereoisomeric form, or mixture thereof, of a compound of the invention.

The term halo refers to fluoro, chloro, bromo, or iodo.

The term alkyl refers to both straight and branched groups, but reference to an individual radical such as "propyl" embraces only the straight chain radical, a branched chain isomer such as "isopropyl" being specifically referred to.

The term "het" refers to a five-(5) or six-(6) membered saturated or unsaturated heterocyclic ring having 1, 2, or 3 heteroatoms selected from the group consisting of oxygen, sulfur, and nitrogen, which is optionally fused to a benzene ring. Examples of unsaturated "het" include pyridine, thiophene, furan, pyrazoline, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 4-oxo-2-imidazolyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 1,2,3-oxathiazole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-indolyl, 3-indolyl, 3-indazolyl, 2-benzoxazolyl, 2-benzothiazolyl, 2-benzimidazolyl, 2-benzofuranyl, 3-benzofuranyl, benzoisothiazole, benzisoxazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3,-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 3-isothiazolyl, 4-isothiazolyl and 5-isothiazolyl, 1,3,4,-oxadiazole, 4-oxo-2-thiazolinyl, or 5-methyl-1,3,4-thiadiazol-2-yl, thiazoledione, 1,2,3,4-thiatriazole, or 1,2,4-dithiazolone.

Examples of saturated "het" include piperdinyl, piperazinyl, morpholinyl, thiomorpholinyl, azetidinyl, pyrrolidinyl, hydantoin, oxathiolane, oxazolidine, dioxolane, or imidazolidine.

At each occurrence, het may be substituted with one or more group as defined in the summary of the invention or in claims.

Specific and preferred values listed below for radicals, substituents, and ranges, are for illustration only; they do not exclude other defined values or other values within defined ranges for the radicals and substituents.

Specifically, $C_{1-4}$ alkyl, $C_{1-6}$ alkyl and $C_{1-8}$ alkyl can be an alkyl group having one to four, one to six, or one to eight carbon atoms respectively such as, for example, methyl, ethyl, propyl, butyl, pentyl, hexyl, heptyl, octyl and their isomeric forms thereof;

A specific value for Y is —NHC(=W)$R^2$.

A specific value for W is oxygen atom.

A specific value for W is sulfur atom

A specific value for $R^2$ is alkyl.

A specific value for $R^2$ is methyl.

A specific value for $R^2$ is ethyl, dichloromethyl, dichloroethyl, or $NH_2$.

A specific value for $R^1$ is 2-fluoroethyl, glycolyl, methoxyacetyl, oxoethylacetate, or methylaminocarbothioyl.

A specific value for $R^1$ is formyl, oracetyl.

A specific value for X is —$CHR^3$—, wherein $R^3$ is H or $C_{1-4}$alkyl.

A specific value for X is —$SO_2$—.

A specific value for Y is —O-het, —S-het, —NH-het.

A specific value for het is isoxazol-3-yl, isoxazol-5-yl, 1,2,4-oxadiazol-3-yl, isothiazol-3-yl, 1,2,4-thiadiazol-3-yl or 1,2,5-thiadiazol-3-yl.

A specific value for n is 1.

A specific value for n is 2.

A preferred compound of the present invention is a compound of formula IA:

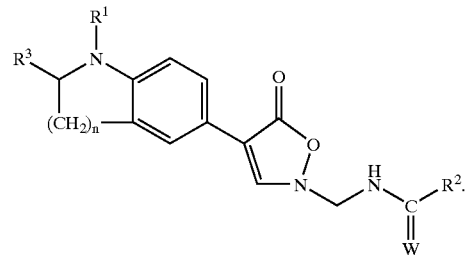

IA

Another preferred compound of the present invention is a compound of formula IB:

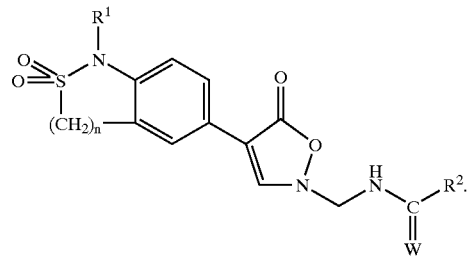

IB

The following Charts I–V describe the preparation of compounds of the present invention. All of the starting materials are prepared by procedures described in these schemes or by procedures that would be well known to one of ordinary skill in organic chemistry. The variables used in the Schemes are as defined below or as in the claims. The compounds of this invention can be prepared in accordance to one or more of the processes discussed below.

Indolines

As shown in Chart I, the requisite 2-alkylindolines (n=1) can be prepared from indole 1 or in the case of the methyl derivative 5 ($R^3$=$CH_3$) purchased from a commercial source. t-Butoxycarbonyl (Boc) protection of the indole nitrogen of 1 using di-t-butyldicarbonate and catalytic dimethylaminopyridine (DMAP) followed by regioselective metalation with n-butyllithium, sec-butyllithium or tert-butyllithium and alkylation with an appropriate electrophile such as alkyl bromides and iodides gives N-Boc-2-alkylindoles 3 ($R^3$ is an alkyl group). Removal of the boc-protecting group affords 2-alkylindoles 4. Reduction with sodiumcyanoborohydride will give the racemic indolines 5. These can be acylated with acetic anhydride under well known conditions to provide the key indoline intermediates 6.

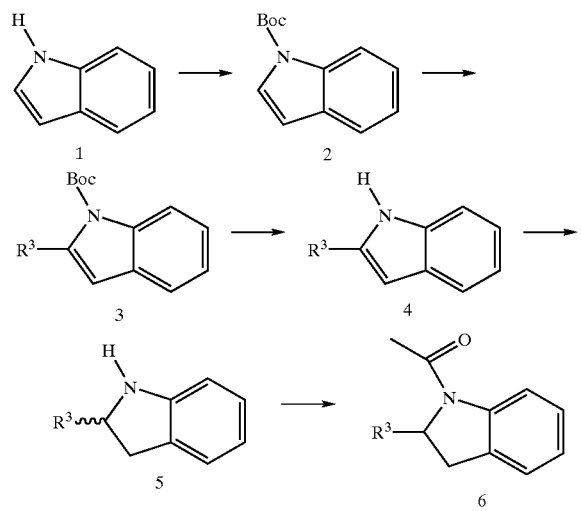

CHART I

In addition, where other groups besides alkyl are desired at the 2-position of the indoline, one can start with commercially available ethyl indole-2-carboxylate 7 (Chart II). Reduction of 7 to the indoline intermediate 8 can be accomplished according to the procedure of Young et.al. (Tetrahedron Lett. 1986, 27, 2409–2410) with magnesium in methanol. Protection of the nitrogen by reaction with acetic anhydride will give 9. Reduction of the ester to the alcohol 10 with an appropriate base such as lithium aluminumhydride, sodium borohydride or di-iso-butylaluminum hydride in a solvent such as diethyl ether or tetrahydrofuran or methanol can then be done at temperatures ranging from −78–60° C. Protection of the hydroxyl group with an appropriate protecting group such as a silyl ether provides indolines 11 (R=Si-(t-Bu)Me$_2$ or SiMe$_3$).

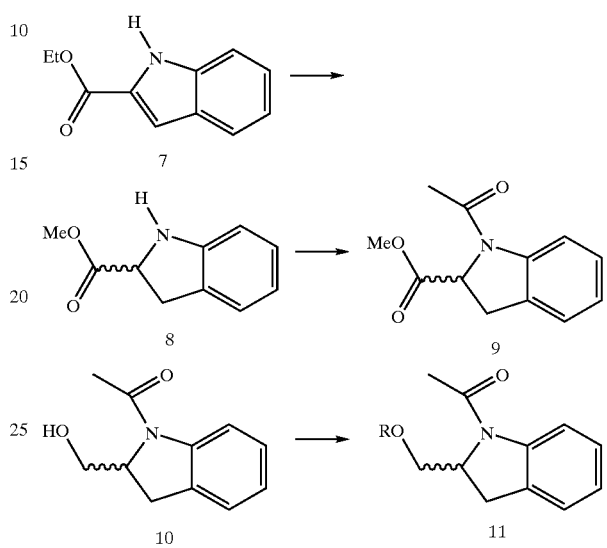

CHART II

Tetrahydroquinolines

Chart III illustrates the synthesis of requisite 2-substituted-tetrahydroquinoline intermediates 20. The desired materials may be prepared from the commercially available quinaldine 12. Oxidation of 12 to the acid 13 can be done according to the procedure of Campbell et al. (J. Am. Chem. Soc. 1946, 68, 1840). Conversion of the acid to the methyl ester in refluxing methanol with catalytic toluenesulfonic acid will give 14. Reduction of the ester to corresponding alcohol 15 with an appropriate reducing agent (sodium borhohydride, lithium aluminumhydride) followed by the protection of the alcohol with a group such as a silyl ether will give 16 (R=Si-(t-Bu)Me$_2$ or SiMe$_3$). The alcohol 15 can also be converted to the aldehyde 18 via Swern oxidation. Olefination (Wittig reaction) of the aldehyde provides alkenes of type 19 (R'=alkyl or H, R"=alkyl or H). Hydrogenation of materials 12, 16 or 19 in the presence of platinum oxide provides the requisite 2-substituted-tetrahydroquinolines 17 (R=alkyl, CH$_2$OSi-(t-Bu)Me$_2$ or CH$_2$OSiMe$_3$) as racemic mixtures. These tetrahydroquinolines can be acylated with acetic anhydride to give the requisite intermediates 20.

CHART III

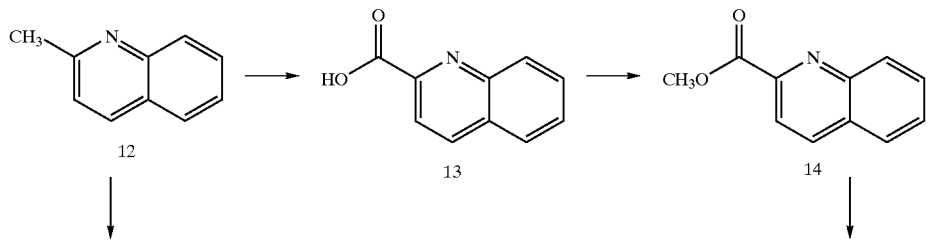

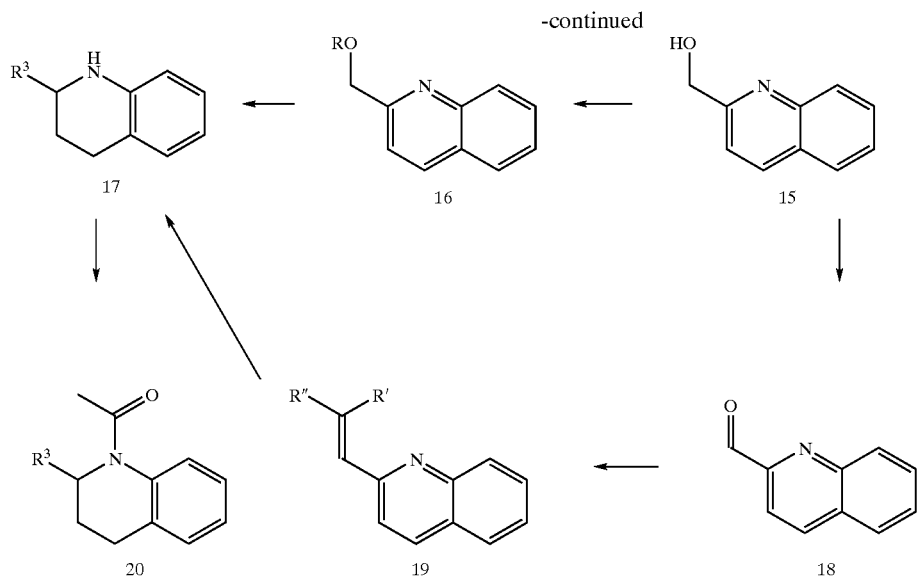

Bicyclic Isoxazolinones

The preparation of the final compounds is outlined in chart IV. The intermediates 6, 11, and 20 can be acylated under Freidel Crafts conditions with acetyl chloride and aluminum chloride in carbon disulfide to provide intermediates 21 (n=1 or 2). Treatment of these materials with thallium (III) nitrate trihydrate and 70% perchloric acid in methanol will yield the esters 22. The N-acetyl group is then replaced with the t-butoxycarbonyl (Boc) protecting group by first refluxing 22 in 6N HCl and methanol to remove the acetate. The intermediate amine is then treated with di-t-butyldicarbonate and triethylamine in dichloromethane to give the Boc-protected esters 23. Treatment of these materials with sodium hydride in ethylformate will yield the formylated derivatives 24. The isoxazolinone rings can be prepared by treating 24 with aqueous hydroxylamine in methanol. The solvent can be stripped off in vacuo and the residue treated with N-(hydroxymethyl)acetamide acetate in dichloromethane with a suitable base such as potassium carbonate. This process yields the intermediates 25 (n=1 or 2, R=alkyl, $CH_2OSi$-(t-Bu)$Me_2$ or $CH_2OSiMe_3$), $R^2$=$CH_3$). The requisite N-(hydroxymethyl)acetamide acetate is prepared as described by WO 0010566 (2000). For example as shown in Chart IV, a compund of formula A (acetamide when $R^2$=$CH_3$) can be reacted with 30–40% formaldehyde solution in water at temperatures ranging from 50–100° C. to give the N-hydroxymethyl acetamide B ($R^2$=$CH_3$). The structure B can be acylated with acetic anhydride with catalytic pyridine to yield the desired reagent C ($R^2$=$CH_3$). Where other groups such as $R^2$ is $C_{2-6}$alkyl, cycloalkyl, O-alkyl, or NHalkyl are desired one skilled in the art can start with different primary carboxamides, carbamates or ureas A ($R^2$=alkyl, O-alkyl, or NH-alkyl) as shown in Chart IV to give various reagents C (R=alkyl, O-alkyl, or NH-alkyl). The starting materials A may be purchased or prepared via methods well known to those skilled in the art.

The Boc-protecting group 25 can then be removed under acidic conditions (trifluoroacetic acid in dichloromethane or HCl(g) in dioxane) to yield the free amino derivatives 26. The nitrogen can then be functionalized by a variety of well known methods to yield the desired analogs. For example, the deprotected materials can be acylated by reactions well known to those skilled in the art to give isoxazolones of structural formula 27 (R'=acyl, W=O). It can also be seen that other acyl derivatives, such as carbamates, can be prepared under similar conditions. In addition, the deprotected materials can be alkylated with alkyl halides and in the presence of appropriate bases (sodium hydride, triethyl amine, potassium carbonate) in a variety of solvents (dimethylformamide, tetrahydrofuran, acetone) to give isoxazolones of structural formula 27 (R'=alkyl, W=O).

Where other substitution on the 2-position of the indoline is desired, the protected alcohol derivatives 25 (R=$CH_2OSi$-(t-Bu)$Me_2$ or $CH_2OSiMe_3$) can be deprotected with flouride ion (eg, tetrabutylammonium fluoride). The resulting alcohols 25 (R=$CH_2OH$) can be alkylated with alkyl halides to prepare other ether derivatives 25 (R=$CH_2O$-alkyl) or acylated to give esters 25 (R=$CH_2O$-acyl). Alternatively, they can be activated as sulfonates (R=$CH_2OSO_2CH_3$) and displaced with amine nucleophiles to yield aminomethyl derivatives 25 (R=$CH_2NH_2$ or $CH_2$NHalkyl) which can be acylated, sulfonylated and/or alkylated to give 25 (R=$CH_2$NHCHO, $CH_2$NHCOalkyl, $CH_2$NHSO$_2$alkyl) by chemical methods well known to those trained in the art. Finally, such alcohols may be converted to the fluoro derivative 25 (R=$CH_2F$) via treatment with (diethylamino)sulfur trifluoride. These materials 25 can be converted to the products 27 (W=O) as described above.

The thioamides 27 (W=S) can be prepared by treating 27 (W=O) with Lawesson's reagent in tetrahydrofuran, dioxane or toluene at temperatures ranging from 50–110° C.

CHART IV

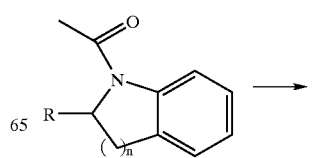

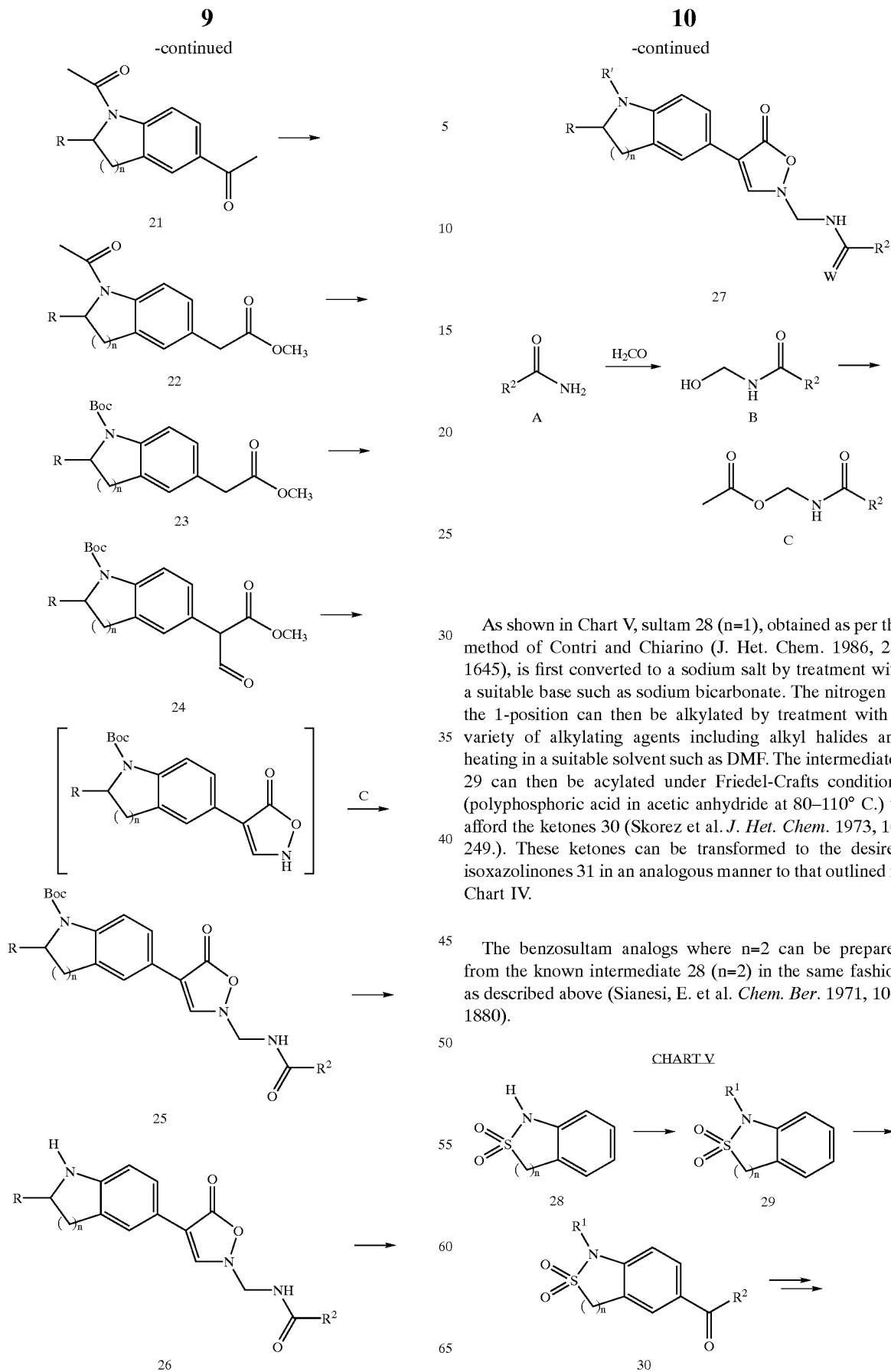

As shown in Chart V, sultam 28 (n=1), obtained as per the method of Contri and Chiarino (J. Het. Chem. 1986, 23, 1645), is first converted to a sodium salt by treatment with a suitable base such as sodium bicarbonate. The nitrogen at the 1-position can then be alkylated by treatment with a variety of alkylating agents including alkyl halides and heating in a suitable solvent such as DMF. The intermediates 29 can then be acylated under Friedel-Crafts conditions (polyphosphoric acid in acetic anhydride at 80–110° C.) to afford the ketones 30 (Skorez et al. *J. Het. Chem.* 1973, 10, 249.). These ketones can be transformed to the desired isoxazolinones 31 in an analogous manner to that outlined in Chart IV.

The benzosultam analogs where n=2 can be prepared from the known intermediate 28 (n=2) in the same fashion as described above (Sianesi, E. et al. *Chem. Ber.* 1971, 104, 1880).

CHART V

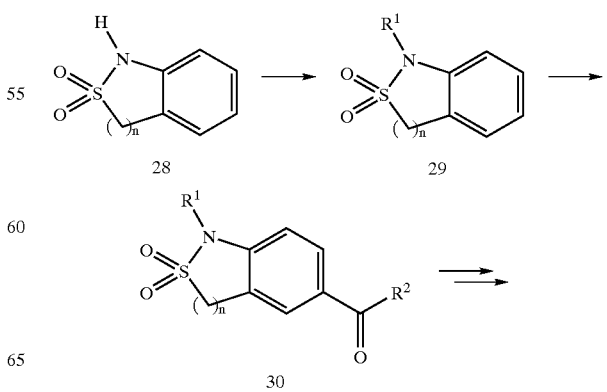

-continued

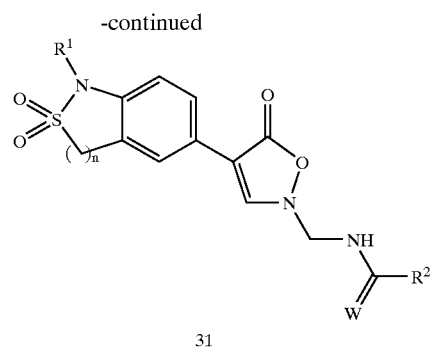

31

These compounds are useful for the treatment of microbial infections, including ophthalmologic infections, in humans and other warm blooded animals, under both parental and oral administration.

The pharmaceutical compositions of this invention may be prepared by combining the compounds of Formula I of this invention with a solid or liquid pharmaceutically acceptable carrier and, optionally, with pharmaceutically acceptable adjuvants and excipient employing standard and conventional techniques. Solid form compositions include powders, tablets, dispersible granules, capsules, cachets and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

Preferably, the pharmaceutical composition is provided employing conventional techniques in unit dosage form containing effective or appropriate amounts of the active component, that is, the compounds of formula I according to this invention.

The quantity of active component, that is the compound of formula I according to this invention, in the pharmaceutical composition and unit dosage form thereof may be varied or adjusted widely depending upon the particular application, the potency of the particular compound and the desired concentration. Generally, the quantity of active component will range between 0.5% to 90% by weight of the composition.

In therapeutic use for treating, or combating, bacterial infections in warm-blooded animals, the compounds or pharmaceutical compositions thereof will be administered orally, topically, transdermally, and/or parenterally at a dosage to obtain and maintain a concentration, that is, an amount, or blood-level of active component in the animal undergoing treatment which will be antibacterially effective. Generally, such antibacterially effective amount of dosage of active component will be in the range of about 0.1 to about 100, more preferably about 3.0 to about 50 mg/kg of body weight/day. It is to be understood that the dosages may vary depending upon the requirements of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., two to four times per day.

The compounds of formula I according to this invention are administered parenterally, i.e., by injection, for example, by intravenous injection or by other parenteral routes of administration. Pharmaceutical compositions for parenteral administration will generally contain a pharmaceutically acceptable amount of the compound according to formula I as a soluble salt (acid addition salt or base salt) dissolved in a pharmaceutically acceptable liquid carrier such as, for example, water-for-injection and a buffer to provide a suitably buffered isotonic solution, for example, having a pH of about 3.5–6. Suitable buffering agents include, for example, trisodium orthophosphate, sodium bicarbonate, sodium citrate, N-methylglucamine, L(+)-lysine and L(+)-arginine to name but a few representative buffering agents. The compounds according to formula I generally will be dissolved in the carrier in an amount sufficient to provide a pharmaceutically acceptable injectable concentration in the range of about 1 mg/ml to about 400 mg/ml of solution. The resulting liquid pharmaceutical composition will be administered so as to obtain the above-mentioned antibacterially effective amount of dosage. The compounds of formula I according to this invention are advantageously administered orally in solid and liquid dosage forms.

The isoxazolinone antibacterial agents of this invention have useful activity against a variety of organisms. The in vitro activity of compounds of this invention can be assessed by standard testing procedures such as the determination of minimum inhibitory concentration (MIC) by agar dilution as described in "Approved Standard. Methods for Dilution Anti microbial Susceptibility Tests for Bacteria That Grow Aerobically", 3rd. ed., published 1993 by the National Committee for Clinical Laboratory Standards, Villanova, Pa., USA. The activity of compounds of this invention against *Staphylococcus aureus*, is shown in Table 1.

TABLE 1

| Antibacterial Activity, Minimum Inhibitory Concentration ($\mu$g/mL) | |
|---|---|
| EXAMPLE # | S.A. |
| 1 | 2 |
| vancomycin | 1 |

S.A is Methicillin-susceptible *S. aureus* UC®9213.
Minimum inhibitory concentration refers to lowest concentration of drug ($\mu$g/mL) that inhibits visible growth of the organism.

EXAMPLE 1
N-{[4-(N-formyl-2-methylindolinyl)-5-oxo-isoxazol-2-yl]methyl}acetamide

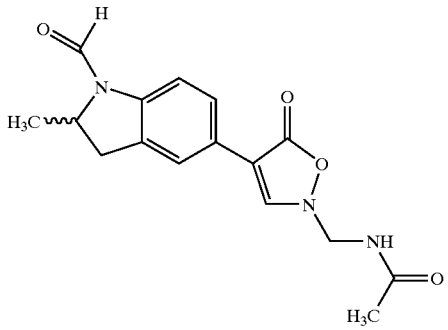

Step 1 Preparation of N-acetyl-2-methylindoline

To a mixture of 2-methylindoline (20.0 g, 0.15 mol) and dimethylaminopyridine (500 mg, 5 mmol) in pyridine (50 mL) at room temperature is added acetic anhydride (20 mL). The mixture is stirred at ambient temperature for 18 h, diluted with ethyl acetate, washed with 1 N aqueous hydrochloric acid, water and brine, then dried over anhydrous sodium sulfate, filtered, and concentrated in vacuo to give 26.3 g (100%) of the title compound as an amber oil. MS (ESI+) m/z 176.1 (M+H).

Step 2 Preparation of N-acetyl-2-methylindolin-5-yl ethanone

To a mixture of the compound from Step 1 (2.0 g, 11.4 mmol) and aluminum chloride (7.0 g, 52 mmol) in carbon disulfide (20 mL) is added acetyl chloride (1.2 mL, 17.1 mmol). The mixture is heated at 50° C. for 72 h, cooled, quenched with ice water then diluted with ethyl acetate and washed with water and brine, dried over anhydrous sodium sulfate, filtered, concentrated, and chromatographed on silica gel eluting with 40–50% ethyl acetate in heptane to give 2.4 g (97%) of the title compound as a off-white solid. MS (ESI+) m/z 217.1 (M+H). Anal. Calcd for $C_{13}H_{15}NO_2$: C, 71.87; H, 6.96; N, 6.45. Found: C, 71.78; H, 6.98; N, 6.43.

Step 3 Preparation of methyl N-acetyl-2-methylindolin-5-yl acetate

The title compound from Step 2 (2.5 g, 11.4 mmol) and thallium (III) nitrate trihydrate (3.4 g, 12.7 mmol) in methanol (50 mL) are treated with 70% perchloric acid (7.5 mL) and stirred 18 h at room temperature. The mixture is filtered through celite, concentrated in vacuo, diluted with water and extracted with dichloromethane. The organics are washed with water and brine, dried over anhydrous sodium sulfate, filtered, concentrated and chromatographed on silica gel eluting with 50% ethyl acetate in heptane to give 1.40 g (49%) of the title compound as yellow oil. MS (ESI+) m/z 248.1 (M+H).

Step 4 Preparation of methyl N-[(t-butyl)oxycarbonyl]-2-methylindolin-5-yl acetate.

The compound from Step 3 (1.35 g, 5.5 mmol) and 6 N aqueous hydrochloric acid in methanol (20 mL) are refluxed for 18 h, cooled, concentrated to remove the methanol and poured into saturated aqueous sodium bicarbonate, then extracted with dichloromethane, dried over anhydrous sodium sulfate, filtered and concentrated. The resulting oil is dissolved in dichloromethane (20 mL) and treated with triethylamine (1.3 mL) and di-t-butyl dicarbonate (1.3 g, 6.0 mmol). After stirring 18 h at room temperature the mixture is washed with water and brine, dried over anhydrous sodium sulfate, filtered, concentrated, and chromatographed on silica gel eluting with 15% ethyl acetate in heptane to give 1.04 g, (62%) of the title compound as a colorless oil. MS (ESI+) m/z 306.1 (M+H).

Step 5 Preparation of ethyl N-[(t-butyl)oxycarbonyl]-α-formyl-2-methylindolin-5-yl acetate.

60% sodium hydride in oil (550 mg, 13 mmol) is added at room temperature to a solution of the compound from Step 4 (1.00 g, 3.3 mmol) in ethyl formate (20 mL). The mixture is stirred at ambient temperature for 3 h, quenched with water, extracted with dichloromethane, which is then dried over anhydrous sodium sulfate, filtered, concentrated, and chromatographed on silica gel eluting with 20% ethyl acetate in heptane to give 830 mg (73%) of the title compound as a yellow oil. MS (ESI+) m/z 348.1 (M+H).

Step 6 Preparation of N-[4-({N-[(t-butyl)oxycarbonyl]-2-methylindolin-5-yl}-5-oxo-isoxazolinyl)methyl]acetamide.

The compound form Step 5 (700 mg, 2.0 mmol) in methanol (20 mL) is treated with 50% aqueous hydroxylamine (1.4 mL, 20 mmol), stirred at room temperature for 3 h, then concentrated in vacuo. This residue is suspended in dichloromethane (20 mL) and treated with potassium carbonate (1.5 g, 11 mmol) and N-(hydroxymethyl)acetamide acetate (1.4 g, 10.6 mmol). The mixture is stirred at room temperature 18 h, poured into water, extracted with dichloromethane, dried over anhydrous sodium sulfate, filtered, concentrated, and chromatographed on silica gel eluting with 5% methanol in dichloromethane to give 360 mg (46%) of the title compound as a white solid. $^1$H NMR (300 MHz, CDCl$_3$) δ 8.16 (s, 1H), 7.5 (m, 2H), 7.03 (t, J=7.0 Hz, 1H), 5.07 (d, J=7.0 Hz, 2H), 4.53 (bs, 1H), 3.38 (dd, J=10.3, 18.0 Hz, 1H), 2.64 (d, J=16.0 Hz, 1H), 2.00 (s, 2H), 1.58 (s, 9H), 1.30 (d, J=7.0 Hz, 3H); MS (ESI–) m/z 422.0 (M+HCl). HRMS (FAB) calcd for $C_{20}H_{25}N_3O_5+H_1$ 388.1872, found 388.1875.

Step 7 Preparation of N-[4-(2-methylindolinyl-5-oxo-isoxazolin-5-yl)methyl]acetamide.

To a solution of the compound from Step 6 (65 mg, 0.17 mmol) in dichloromethane (3 mL) is added trifluoroacetic acid (1 mL). The solution is stirred at room temperature for 2 h, washed with saturated aqueous sodium bicarbonate, brine, dried over anhydrous sodium sulfate, filtered, concentrated in vauo to give 43 mg (89%) of the title compound as a brown solid. MS (ESI+) m/z 288.1 (M+H). HRMS (FAB) calcd for $C_{15}H_{17}N_3O_3+H_1$ 288.1348, found 288.1351.

Step 8 Preparation of N-{[4-(N-formyl-2-methylindolin-5-yl)-5-oxo-isoxazol-2-yl]methyl}acetamide.

Acetic anhydride (50 μL) and 100% formic acid (40 μL) are heated at 50° C. for 1 h under nitrogen, cooled to room temperature, diluted with THF (1 mL) and then treated with the compound from Step 7 (36 mg, 0.12 mmol) in THF (2 mL). The solution is stirred for 5 h, washed with water and brine, dried over anhydrous sodium sulfate, filtered, concentrated, and chromatographed on silica gel eluting with 5% methanol in dichloromethane to give 25 mg (64%) of the title compound as an off-white solid. MS (ESI+) m/z 316.0 (M+H). HRMS (FAB) calcd for $C_{16}H_{17}N_3O_4+H_1$ 316.1297, found 316.1306.

We claim:
1. A compound of formula I

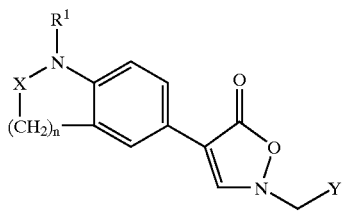

or a pharmaceutically acceptable salt thereof wherein
Y is
  a) —NHC(=W)R$^2$, or
  b) —O-het, —S-het, or —NH-het;
W is
  a) O, or
  b) S;
X is
  a) —S(=O)$_m$—, or
  b) —CHR$^3$—;
R$^1$ is
  a) C$_{1-8}$ alkyl,
  b) —C(=O)R$^4$, or
  c) —C(=S)NHC$_{1-4}$ alkyl;
R$^2$ is
  a) H,
  b) C$_{1-6}$ alkyl,
  c) cyclopropyl,
  d) —OC$_{1-4}$ alkyl,
  e) —NH$_2$,
  f) —NHC$_{1-6}$ alkyl, or
  g) —N(C$_{1-6}$ alkyl)$_2$;
R$^3$ is H, or C$_{1-4}$ alkyl;
R$^4$ is
  a) H,
  b) C$_{1-6}$ alkyl, or
  c) —CH$_2$OC(=O)C$_{1-4}$ alkyl;
at each occurrence above, alkyl is optionally substituted with one or more R$^5$;
R$^5$ is
  a) halo,
  b) CN,
  c) NO$_2$,
  d) C$_{1-6}$ alkyl,
  e) phenyl,
  f) OR$^6$,
  g) C(=O)R$^6$,
  h) OC(=O)R$^6$,
  i) C(=O)OR$^6$,
  j) S(=O)$_m$R$^6$,
  k) S(=O)$_m$NR$^6$R$^6$,
  l) NHC(=O)R$^6$,
  m) C(=O)NR$^6$R$^6$, or
  n) NR$^6$R$^6$,
R$^6$ is independently H, C$_{1-6}$alkyl, phenyl, or het;
het is a C-linked five-(5) or six-(6) membered saturated or unsaturated heterocyclic ring having 1, 2, or 3 heteroatoms selected from the group consisting of oxygen, sulfur, and nitrogen, which is optionally fused to a benzene ring; wherein het is optionally substituted with one or more halo, CN, NO$_2$, C$_{1-6}$ alkyl, OR$^6$, phenyl, S(=O)$_m$R$^6$, C(=O)R$^6$, OC(=O)R$^6$, NHC(=O)R$^6$, or NR$^6$R$^6$, oxo, or oxime;
m is 0, 1 or 2; and n is 1 or 2.
2. A compound of claim 1 which is a compound of formula IA

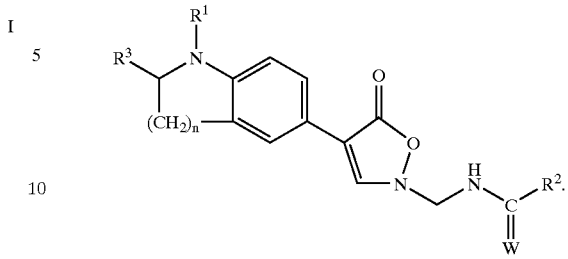

3. A compound of claim 1 which is a compound of formula IB

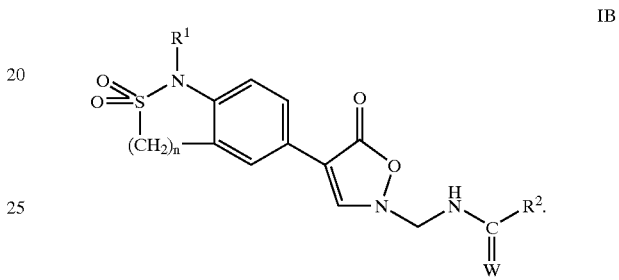

4. A compound of claim 2 or 3 wherin R$^2$ is C$_{1-6}$alkyl.
5. A compound of claim 2 or 3 wherin R$^2$ is methyl.
6. A compound of claim 2 or 3 wherein R$^1$ is formyl or acetyl.
7. A compound of claim 2 or 3 wherein n is 1.
8. A compound of claim 2 or 3 wherein n is 2.
9. A compound of claim 2 or 3 wherein R$^1$ is 2-fluoroethyl, glycolyl, methoxyacetyl, oxoethylacetate, or methylaminocarbothioyl.
10. A compound of claim 2, wherein R$^3$ is methyl.
11. A compound of claim 1 which N-{[4-(N-formyl-2-methylindolinyl)-5-oxo-isoxazol-2-yl]methyl}acetamide.
12. A compound of claim 1 wherein het is isoxazol-3-yl, isoxazol-5-yl, 1,2,4-oxadiazol-3-yl, isothiazol-3-yl, 1,2,4-thiadiazol-3-yl or 1,2,5-thiadiazol-3-yl.
13. A method for treating microbial infections in patients comprising: administering to a human or warm blood animals in need thereof an effective amount of a compound of claim 1.
14. The method of claim 13 wherein said compound of formula I is administered orally, parenterally, transdermally, or topically in a pharmaceutical composition.
15. The method of claim 13 wherein said compound is administered in an amount of from about 0.1 to about 100 mg/kg of body weight/day.
16. The method of claim 13 wherein said compound is administered in an amount of from about 1 to about 50 mg/kg of body weight/day.
17. A method for treating microbial infections of claim 13 wherein the infection is skin infection.
18. A method for treating microbial infections of claim 13 wherein the infection is eye infection.
19. A pharmaceutical composition comprising a compound of claim 1 and a pharmaceutically acceptable carrier.

* * * * *